United States Patent
Hodge et al.

(10) Patent No.: US 9,737,549 B2
(45) Date of Patent: *Aug. 22, 2017

(54) FORMULATIONS OF DEOXYCHOLIC ACID AND SALTS THEREOF

(71) Applicant: Kythera Biopharmaceuticals, Inc., Calabasas, CA (US)

(72) Inventors: Robert Emil Hodge, McPherson, KS (US); Jeffrey Douglas Webster, Thousand Oaks, CA (US); Robert M. Moriarty, Michiana Shores, IN (US)

(73) Assignee: Kythera Biopharmaceuticals, Inc., Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/091,109

(22) Filed: Nov. 26, 2013

(65) Prior Publication Data

US 2014/0148429 A1 May 29, 2014

Related U.S. Application Data

(63) Continuation of application No. 13/207,337, filed on Aug. 10, 2011, now Pat. No. 8,653,058, and a (Continued)

(51) Int. Cl.
*A61K 31/57* (2006.01)
*A61K 31/575* (2006.01)
(Continued)

(52) U.S. Cl.
CPC .......... *A61K 31/575* (2013.01); *A61K 9/0019* (2013.01); *A61K 47/02* (2013.01); *A61K 47/10* (2013.01)

(58) Field of Classification Search
None
See application file for complete search history.

(56) References Cited

U.S. PATENT DOCUMENTS

| 4,113,882 A | 9/1978 | Okazaki et al. |
| 4,117,121 A | 9/1978 | Gallo-Torres et al. |

(Continued)

FOREIGN PATENT DOCUMENTS

| CA | 2033725 | 5/2001 |
| CA | 2551474 | 7/2005 |

(Continued)

OTHER PUBLICATIONS

Sigma RIPA Buffer (available before Apr. 5, 2007).*
(Continued)

*Primary Examiner* — Anna Pagonakis
(74) *Attorney, Agent, or Firm* — Foley & Lardner LLP

(57) ABSTRACT

The present application is directed to an aqueous pharmaceutical composition comprising from about 0.4% w/v to less than about 2% w/v of a salt of deoxycholic acid, wherein the composition is maintained at a pH from about 8.1 to about 8.5 such that the composition is stabilized against precipitation. Also disclosed herein, are methods for stabilizing an aqueous pharmaceutical composition comprising from about 0.4% w/v to less than about 2% w/v of a salt of deoxycholic acid against precipitation, said method comprising maintaining pH of the solution from about 8.1 to about 8.5.

6 Claims, 4 Drawing Sheets

Related U.S. Application Data continuation-in-part of application No. PCT/US2011/031284, filed on Apr. 5, 2011.

(60) Provisional application No. 61/483,008, filed on May 5, 2011.

(51) Int. Cl.
  *A61K 9/00* (2006.01)
  *A61K 47/02* (2006.01)
  *A61K 47/10* (2017.01)

(56) References Cited

U.S. PATENT DOCUMENTS

| | | | |
|---|---|---|---|
| 4,158,707 A | 6/1979 | Steffen et al. | |
| 4,664,910 A | 5/1987 | Caserio et al. | |
| 4,681,876 A | 7/1987 | Marples et al. | |
| 4,722,888 A * | 2/1988 | Broder | C07K 16/1036 422/430 |
| 4,851,435 A | 7/1989 | Sauer et al. | |
| 4,866,044 A | 9/1989 | Sato et al. | |
| 4,994,439 A | 2/1991 | Longenecker et al. | |
| 5,085,864 A | 2/1992 | Cannon et al. | |
| 5,288,498 A | 2/1994 | Stanley et al. | |
| 5,326,562 A | 7/1994 | Scott | |
| 5,344,822 A | 9/1994 | Levine et al. | |
| 5,371,104 A | 12/1994 | Feigenbaum | |
| 5,376,646 A | 12/1994 | Pittrof et al. | |
| 5,395,545 A | 3/1995 | Fischer et al. | |
| 5,506,218 A | 4/1996 | Parker et al. | |
| 5,603,932 A | 2/1997 | Blaas et al. | |
| 5,616,342 A | 4/1997 | Lyons | |
| 5,674,855 A | 10/1997 | Levine et al. | |
| 5,747,066 A | 5/1998 | Pittrof et al. | |
| 5,759,445 A | 6/1998 | Yamamoto et al. | |
| 5,849,883 A | 12/1998 | Boone et al. | |
| 5,863,554 A | 1/1999 | Illum | |
| 5,876,721 A | 3/1999 | Alexander et al. | |
| 5,891,083 A | 4/1999 | Capella et al. | |
| 5,914,390 A | 6/1999 | Nathan et al. | |
| 5,942,248 A | 8/1999 | Barnwell | |
| 5,952,313 A | 9/1999 | Carlson | |
| 5,952,392 A | 9/1999 | Katz et al. | |
| 6,025,396 A | 2/2000 | Kim et al. | |
| 6,120,805 A | 9/2000 | Spenlehauer et al. | |
| 6,197,327 B1 | 3/2001 | Harrison et al. | |
| 6,221,378 B1 | 4/2001 | Modi | |
| 6,225,343 B1 | 5/2001 | Behl et al. | |
| 6,251,428 B1 | 6/2001 | Yoo | |
| 6,255,502 B1 | 7/2001 | Penkler et al. | |
| 6,294,192 B1 | 9/2001 | Patel et al. | |
| 6,313,128 B1 | 11/2001 | Blanc-Ferras et al. | |
| 6,315,984 B1 | 11/2001 | Modi | |
| 6,342,489 B1 | 1/2002 | Palmieri et al. | |
| 6,350,458 B1 | 2/2002 | Modi | |
| 6,375,975 B1 | 4/2002 | Modi | |
| 6,383,471 B1 | 5/2002 | Chen et al. | |
| 6,416,779 B1 | 7/2002 | D'Augustine et al. | |
| 6,417,179 B1 * | 7/2002 | Burkhart et al. | 514/178 |
| 6,451,286 B1 | 9/2002 | Modi | |
| 6,489,312 B1 | 12/2002 | Stogniew et al. | |
| 6,537,561 B1 | 3/2003 | Fukui et al. | |
| 6,544,972 B1 | 4/2003 | Steer et al. | |
| 6,663,885 B1 | 12/2003 | Hager et al. | |
| 6,713,470 B2 | 3/2004 | Jackson | |
| 6,849,263 B2 | 2/2005 | Modi | |
| 6,884,768 B2 | 4/2005 | Kimura et al. | |
| 7,226,775 B2 | 6/2007 | Mapleson et al. | |
| 7,303,768 B2 | 12/2007 | Yoo | |
| 7,538,093 B2 | 5/2009 | Engler et al. | |
| 7,622,130 B2 | 11/2009 | Kolodney et al. | |
| 7,754,230 B2 | 7/2010 | Kolodney et al. | |
| 8,101,593 B2 * | 1/2012 | Hodge et al. | 514/182 |
| 8,258,146 B2 | 9/2012 | Morita et al. | |
| 8,298,556 B2 | 10/2012 | Kolodney et al. | |
| 8,367,649 B2 * | 2/2013 | Hodge et al. | 514/182 |
| 8,653,058 B2 * | 2/2014 | Hodge et al. | 514/182 |
| 8,846,066 B2 | 9/2014 | Kolodney et al. | |
| 9,186,364 B2 * | 11/2015 | Hodge | A61K 31/575 |
| 2001/0051595 A1 | 12/2001 | Lyons et al. | |
| 2002/0028766 A1 | 3/2002 | Papadimitriou | |
| 2002/0031558 A1 | 3/2002 | Yoo | |
| 2002/0032159 A1 | 3/2002 | Maruyama et al. | |
| 2002/0058010 A1 | 5/2002 | Picard-Lesboueyries et al. | |
| 2002/0107291 A1 | 8/2002 | De Tommaso | |
| 2002/0168402 A1 | 11/2002 | Kipp et al. | |
| 2003/0027833 A1 | 2/2003 | Cleary et al. | |
| 2003/0035831 A1 | 2/2003 | Modi | |
| 2003/0054981 A1 | 3/2003 | Milton et al. | |
| 2003/0064097 A1 | 4/2003 | Patel et al. | |
| 2003/0072807 A1 | 4/2003 | Wong et al. | |
| 2003/0077329 A1 | 4/2003 | Kipp et al. | |
| 2003/0161886 A1 | 8/2003 | Dickinson et al. | |
| 2003/0186933 A1 | 10/2003 | Yoo | |
| 2003/0219472 A1 | 11/2003 | Pauletti et al. | |
| 2004/0022862 A1 | 2/2004 | Kipp et al. | |
| 2004/0038952 A1 | 2/2004 | Feher | |
| 2004/0067919 A1 | 4/2004 | Jee | |
| 2004/0096494 A1 | 5/2004 | Siekmann et al. | |
| 2004/0101569 A1 | 5/2004 | Rang | |
| 2004/0115255 A1 | 6/2004 | Leigh et al. | |
| 2004/0141949 A1 | 7/2004 | Rosenthal et al. | |
| 2004/0161407 A1 | 8/2004 | Kimura et al. | |
| 2004/0201117 A1 | 10/2004 | Anderson | |
| 2004/0213855 A1 | 10/2004 | Pettersson et al. | |
| 2004/0220283 A1 | 11/2004 | Zhang et al. | |
| 2005/0019404 A1 | 1/2005 | Sung et al. | |
| 2005/0048126 A1 | 3/2005 | Rabinow et al. | |
| 2005/0079228 A1 | 4/2005 | Jaiswal et al. | |
| 2005/0089555 A1 | 4/2005 | Boderke et al. | |
| 2005/0123582 A1 | 6/2005 | Sung et al. | |
| 2005/0143347 A1 | 6/2005 | Boderke et al. | |
| 2005/0158408 A1 | 7/2005 | Yoo | |
| 2005/0163821 A1 | 7/2005 | Sung et al. | |
| 2005/0261258 A1 | 11/2005 | Kolodney et al. | |
| 2005/0266065 A1 | 12/2005 | Perrier et al. | |
| 2005/0267080 A1 | 12/2005 | Kolodney et al. | |
| 2005/0287199 A1 | 12/2005 | Denney et al. | |
| 2006/0074057 A1 | 4/2006 | Marchewitz | |
| 2006/0127468 A1 | 6/2006 | Kolodney et al. | |
| 2006/0154906 A1 | 7/2006 | Kolodney et al. | |
| 2006/0222673 A1 | 10/2006 | Chern et al. | |
| 2006/0222695 A1 | 10/2006 | Zadini et al. | |
| 2008/0318870 A1 | 12/2008 | Moriarty et al. | |
| 2009/0270642 A1 | 10/2009 | Prasad et al. | |
| 2009/0275545 A1 | 11/2009 | Boderke et al. | |
| 2010/0292650 A1 | 11/2010 | Kolodney et al. | |
| 2011/0002896 A1 | 1/2011 | Kolodney et al. | |
| 2012/0237492 A1 | 9/2012 | Walker | |
| 2013/0109282 A1 * | 5/2013 | Lewkoski et al. | 451/178 |
| 2013/0190282 A1 | 7/2013 | Hodge et al. | |
| 2014/0004206 A1 | 1/2014 | Kolodney et al. | |
| 2014/0155364 A1 * | 6/2014 | Hodge | A61K 31/57 514/182 |
| 2015/0051182 A1 | 2/2015 | Kolodney et al. | |

FOREIGN PATENT DOCUMENTS

| | | |
|---|---|---|
| CN | 1348360 A | 5/2002 |
| EP | 0 208 519 | 1/1987 |
| EP | 0 426 029 | 5/1991 |
| EP | 0 439 042 | 6/1995 |
| EP | 0 439 513 | 3/1996 |
| EP | 1 111 390 | 6/2001 |
| EP | 0 730 860 | 1/2002 |
| EP | 0 806 940 | 4/2003 |
| EP | 1 005 324 | 3/2005 |
| JP | 61-158995 | 7/1986 |
| JP | 03-048622 | 3/1991 |
| JP | 04-235918 | 8/1992 |
| JP | 11-240835 | 9/1999 |
| JP | 2007-515439 | 6/2007 |
| JP | 2007-515494 | 6/2007 |

(56) References Cited

FOREIGN PATENT DOCUMENTS

| | | |
|---|---|---|
| JP | 2007-538104 | 12/2007 |
| JP | 2010-222283 | 10/2010 |
| WO | WO-90/12583 | 11/1990 |
| WO | WO 93/05811 | 4/1993 |
| WO | WO-94/04177 | 3/1994 |
| WO | WO-99/15152 | 4/1999 |
| WO | WO-00/13029 | 3/2000 |
| WO | WO-02/058610 | 8/2002 |
| WO | WO-03/018134 | 3/2003 |
| WO | WO-03/082340 | 10/2003 |
| WO | WO-03/094894 | 11/2003 |
| WO | WO-2004/010941 | 2/2004 |
| WO | WO-2004/039326 | 5/2004 |
| WO | WO-2005/020894 | 3/2005 |
| WO | WO-2005/061004 | 7/2005 |
| WO | WO-2005/063169 | 7/2005 |
| WO | WO-2005/063205 | 7/2005 |
| WO | WO 2005/112942 | 12/2005 |
| WO | WO-2005/117832 | 12/2005 |
| WO | WO 2005/117900 | 12/2005 |
| WO | WO-2006/007675 | 1/2006 |
| WO | WO-2006/133160 | 12/2006 |
| WO | WO-2011/075701 | 6/2011 |

OTHER PUBLICATIONS

Shimazawa et al. (Mol. Vis. 13: 578-587, 2007).*
U.S. Appl. No. 11/710,601, filed Feb. 23, 2007, Burkhart et al.
U.S. Appl. No. 12/062,445, filed Apr. 3, 2008, Kolodney et al.
U.S. Appl. No. 12/397,229, filed Mar. 3, 2009, Hodge et al.
U.S. Appl. No. 13/753,366, filed Jan. 29, 2013, Hodge et al.
Ablon et al. Treatment of Lower Eyelid Fat Pads Using Phosphatidylcholine: Clinical Trial and Review, Dermatol. Surg. (2004) 30(3):422-427.
Alkan-Onyuksel et al. A mixed micellar formulation suitable for the parenteral administration of taxol. Pharm Res (1994) 11(2):206-212.
Almgren M. Mixed micelles and other structures in the solubilization of bilayer lipid membranes by surfactants. Biochim Biophys Acta (2000)1508:146-163.
Asaadi et al. Mesoplasty: a new approach to non-surgical liposculpture. Plastic Surgery 2004, Oct. 10, 2004, Philadelphia, PA.
ASAPS. American Society for Aesthetic Plastic Surgery. Lipoplasty (liposuction) without surgery?, Oct. 2002.
Author Unknown. Health Alert: Lipostabil. http://kyw.com/health/local.sub.--story.sub.--336152706.html, Dec. 2, 2002.
Author Unknown. Learn about lecithins. Oxford, CT: American Lecithin Company (2003).
Author Unknown. Lipostabil. Rhone-Poulenc Rorer. Cologne, West Germany: Natterman International GMBH (1990).
Author Unknown. Lose those love handles, A CBS HealthWatch Special Report http://cbsnewyork.com/healthwatch/local.sub.--story.sub.--329141707.html, Nov. 25, 2002.
Author Unknown. Love handles can be shrunk without surgery http://www.macleans.ca/topstories/health/article.jsp?content=20040225.sub- .--090843.sub.--4800, Feb. 25, 2004.
Banerjee et al. Differential solubilization of lipids along with membrane proteins by different classes of detergents. Chem Phys Lipids (1995) 77:65-78.
Bates B. Fat dissolving substance injects CCs of controversy. Skin and Allergy News (2003) 34(2).
Bayer Press Release, First Patients enrolled in EU Phase III Clinical Development Program to evaluate ATX-101 for reduction of Submental Fat, (2008).
Bellman B. Phosphatidylcholine reaction. Skin and Allergy News (2003) 34(4).
Bryant R. Controversial mesotherapy: could it be the next botox. Dermatology Times (2004) 1-2.
Buko et al. Hepatic and pancreatic effects of polyenoylphosphatidylcholine in rats with alloxan-induced diabetes. Cell Biochem Function (1996)14:131-137.
Canty et al. Lecithin and choline: research update on health and nutrition. Fort Wayne, IN: Central Soya Company, Inc. (1998).
Chalmers K. Fat loss a needle away. http://surgerynews.neUnews/0204/meso020402.htm, Feb. 1, 2004.
Davidson et al. Limitations of phosphatidylcholine/deoxycholate mixtures for the analysis of phospholipase A2 inhibition and activation: illustration with annexins. Biochimica et Biophysica Acta, (1992) 1127(3):270-276.
Duncan et al. Lipodissolve for Subcutaneous Fat Reduction and Skin Retraction, Aesthetic Surgery Journal (2005) 25(5):530-543.
Duncan et al.: "Injectable therapies for localized fat loss: state of the art.", Clinics in Plastic Surgery, 2011, LNKDPUBMED:21824545, vol. 38, No. 3, 2011, pp. 489-501.
Durr et al. Investigation on mixed micelle and liposome preparations for parental use on soya phosphatidylcholine. Eur J Pharm Biopharm (1994) 40(3):147-156.
Ebihara et al. Effect of benzyl alcohol on lipid bilayers. A comparisons of bilayer systems. Biophys J (1979) 28:185-196.
Engelke et al. Effect of inhalation anaesthetics on the phase behaviour, permeability and order of phosphatidylcholine bilayers. Biophys Chem (1997)67:127-138.
FDA news release: "FDA issues warning letters for drugs promoted in fat elimination procedure", 2010, Retrieved from the Internet: URL:http://www.fda.gov/NewsEvents/Newsroom/PressAnnouncements/ucm207453.htm [retrieved on Oct. 18, 2011].
Goldman et al. Cecil Textbook of Medicine. St. Louis, MO: W.B. Saunders Co. (2001)21(1):821-833.
Gordon et al. The increase in bilayer fluidity of rat liver plasma membranes achieved by the local anesthetic benzyl alcohol affects the activity of intrinsic membrane enzymes. J Biol Chem (1980) 255(10):4519-4527.
Gustafson et al. Influence of organic solvent mixtures on biological membranes. Br J Ind Med (1985) 42:591-595.
Hammad et al. Increasing drug solubility by means of bile salt-phosphatidylcholine-based mixed micelles. Eur J Pharm Biopharm (1998) 46:361-367.
Hasengschwandtner F. Phosphatidylcholine treatment to induce lipolysis. Journal of Cosmetic Dermatology (2005) 4:308-313.
Heerklotz et al. Correlation of membrane/water partition coefficients of detergents with the critical micelle concentration. Biophys J (2000) 78:2435-2440.
Hexsel et al. Phosphatidylcholine in the treatment of localized fat, J. Drugs Dermatol. (2003) 2(5):511-518.
Hofmann et al., "Bile acid solubility and precipitation in vitro and in vivo: the role of conjugation, pH, and Ca2+ ions", Journal of Lipid Research, vol. 33, pp. 617-626 (1992).
Igimi et al., "pH-Solubility relations of chenodeoxycholic and ursodeoxycholic acids: physical-chemical basis for dissimilar solution and membrane phenomena", Journal of Lipid Research, vol. 21, pp. 72-90 (1980).
Jones MN. Surfactants in membrane solubilisation. Int J Pharm (1999)177:137-59.
Kawanaka et al., Kan Tan Sui, (2002) 44(4): 521-526 with partial translation.
Kern et al., "Regulation of Lipoprotein Lipase Immunoreactive Mass in Isolated Human Adipocytes", J. Clin. Invest., vol. 81, pp. 398-406 (1988).
Klein et al. A New Method to Quantify the Effect After Subcutaneous Injection of Lipolytic Substances. Aesth Plast Surg. (2008) 32:667-672.
Kolonin et al. "Reversal of obesity by targeted ablation of adipose tissue" Nature Medicine, Nature Publishing Group, (2004) 10(6): 625-632.
Kythera Biopharmaceuticals: "Evaluation of safety and efficacy of ATX-101 in the reduction of submental fat", 2011, Retrieved from the Internet: URL:http://clinicaltrials.gov/ct2/show/NCT01305577, [retrieved on Oct. 18, 2011].

(56) References Cited

OTHER PUBLICATIONS

Kythera Newsroom. Two Phase 2 studies with ATX-101—study results demonstrated statistically significant reduction in patients' unwanted submental fat. Kythera Biopharmaceuticals, Inc. (2009) 1-2.
Landman B. Beyond Botox. Cosmetic Surgery Guide 2003 http://newyorkmetro.com/nymetro/health/bestdoctors/cosmeticsurgery/2003/n- .sub.--9281/index.html.
Lester et al. Action of organic solvents on protein kinase C. Eur J Pharmacol (1991) 206:301-308.
Lichtenberg D. Characterization of the solubilization of lipid bilayers by surfactants. Biochim Biophys Acta (1985) 821:470-478.
Lichtenberg et al. Solubilization of phospholipids by detergents. Structural and kinetic aspects. Biochim Biophys Acta (1983) 737:285-304.
Lichtenberg et al. Structural and kinetic studies on the solubilization of lecithin by sodium deoxycholate. Biochemistry (1979) 18(16):3517-3525.
Lieber et al. Phosphatidylcholine protects against fibrosis and cirrhosis in the baboon. Gastroenterology (1994)106:152-159.
McCaslin, "Detergent Properties", Encyclopedia of Biological Chemistry, vol. 1, pp. 577-581 (2004).
Milovic et al. Effects of deoxycholate on human colon cancer cells: apoptosis or proliferation. European Journal of Clinical Investigation. (2002) 32(1):29-34.
Moy LS. Phosphatidylcholine injections: a study measuring decreased subcutaneous fat thickness. Combined Annual Meeting of the American Society for Dermatologic Surgery and the American Society of Mohs Micrographic Surgery and Cutaneous Oncology, San Diego, CA Sep. 30-Oct. 3, 2004.
Parnham et al. Phospholipids and liposomes—safety for cosmetical and pharmaceutical use. Nattermann Phospholipid GMBH Scientific Publication (1995)No. 2:1-56.
Powell et al. Bile acid hydrophobicity is correlated with induction of apoptosis and/or growth arrest in HCT116 cells. Biochem. J. (2001) 356:481-486.
Rittes PG. The use of phosphatidylcholine for correction of localized fat deposits, Aesthetic Plast. Surg. (2003) 27(4):315-318.
Rittes PG. The use of phosphatidylcholine for correction of lower lid bulging due to prominent fat pads. Dermatol Surg (2001) 27:391-392.
Rosenbaum M. An exploratory investigation of the morphology and biochemistry of cellulite, Annual Meeting of American Society for Aesthetic Surgery (1997)101(7):1934-1939.
Rossi et al. Cellulite: a review. JEADV (2000)14:251-262.
Rotunda et al. "Detergent effects of sodium deoxycholate are a major feature of an injectable phosphatidylcholine formulation used for localized fat dissolution". Dermatol. Surgery, (2004) 30(7):1001-1008.
Rotunda et al. "Lipomas treated with subcutaneous deoxycholate injections". J. Am. Acad. Dermatol., (2005) pp. 973-978.
Rotunda et al. "Mesotherapy and Phosphatidylcholine Injections: Historical Clarification and Review" Dermatologic Surgery, (2006) 32: 465-480.
Rotunda et al. Detergent effects of sodium deoxycholate are a major feature of injectable phosphatidylcholine. American Society for Dermatologic Surgery, New Orleans, LA, Oct. 11, 2003.
Rotunda et al., "Randomized double-blind clinical trial of subcutaneously injected deoxycholate versus a phosphatidylcholine-deoxycholate combination for the reduction of submental fat", Dermatologic Surgery, 2009, 35(5):792-803.
Sager S. New fat removal technique getting raves: Is it safe? Does it work? http://abclocal.go.com/wabc/news/wabc.sub.--020703.sub.--mesotherap- y.html, Feb. 7, 2003.
Salti et al. Phosphatidylcholine and Sodium Deoxycholate in the Treatment of Localized Fat: A Double-Blind, Randomized Study. Dermatol Surg. (2008)34:60-66.
Schuck et al. Resistance of cell membranes to different detergents. Proc Natl Acad Sci (2003) 100(10):5795-5800.
Sergio M. Traitment mesotherapique das xanthelasmas a la phophatidilcoline polyinsaturee. Dermatologie (2009) 364-365.
Serra M. Subcutaneous infiltration with phosphatidylcholine solution for treatment of buffalo hump and fatty pads. 3rd Int'l workshop on adverse drug reactions and lipodystrophy in HIV, Athens, Oct. 2001, 115.
SIGMA: Rife Buffer, 2003, retrieved from the internet: URL:http://www.sigmaaldrich.com/etc/medialib/docs/Sigma/Bulletin/r0278bul.Par.0001.File.tmp/r0278bul.pdf.
Singer et al. The fluid mosaic model of the structure of cell membranes. Science (1972) 175:720-731.
Small, "Size and Structure of Bile Salt Micelles. Influence of Structure, Concentration, Counterion Concentration, pH, and Temperature", In Molecular Association in Biological and Related Systems; Goddard, E.; Advances in Chemistry; American Chemical Society: Washington, DC, 31-52, 1968.
Teelmann et al. Preclinical safety evaluation of intravenously administered mixed micelles. Arzneimittelforschung (1984)34:1517-1523.
Toyama M. Next-Gen Liposuction. http://www.time.com/time/europe/forecast2003/html/liposuction.html, Dec. 8, 2002.
Victor S. Phosphatidylcholine works. Skin and Allergy News (2003) 34.
Womack et al., "Detergent Effects on Enzyme Activity and Solubilization of Lipid Bilayer Membranes", Biochimica et Biophysica Acta, 733, pp. 210 215 (1983).
Young, VL. Lipostabil. The effect of phosphatidylcholine on subcutaneous fat. Aesthetic Surg J (2003)23:413-417.
Zeghari et al., "Adipocyte and erythrocyte plasma membrane phospholipid composition and hyperinsulinemia: a study in nondiabetic and diabetic obese women", International Journal of Obesity and Related Metabolic Disorders:Journal of the International Association for the Study of Obesity, 2000, 24(12):1600-1607.
Duncan et al., "Fat Reduction Using Phosphatidylcholine/Sodium Deoxycholate Injections: Standard of Practice", Aesthetic Plastic Surgery, 2008, 32(6):858-872.
Extended European Search Report for Appl. No. 12747416.1, dated Jun. 10, 2014.
Hutchinson, ABC News Medical Unit: "Docs Question Bayer's Injection for Dissolving Double Chin", 2011, Retrieved from Internet: URL:http://abcnews.go.com/Health/WellnessNews/bayer-tests-fat-loss-injection-double-chin/story?id=12600333, [retrieved on May 22, 2014].
Japanese Office Action for Appl. No. 2013-034203, mailed Apr. 17, 2014.
"Deoxycholic acid", Product Information, SIGMA, 2002.
JP Office Action for Application No. 2014-527128 dated Jun. 23, 2015.
Shimazawa et al., "Involvement of ER stress in retinal cell death", Mol Vis, 2007, 13:578-587.

\* cited by examiner

FORMULATIONS OF DEOXYCHOLIC ACID AND SALTS THEREOF

CROSS-REFERENCE TO RELATED APPLICATIONS

This application is a Continuation Application of co-pending U.S. patent application Ser. No. 13/207,337, filed on 10 Aug. 2011; which is a continuation-in-part of PCT Application No. PCT/US2011/031284, filed on 5 Apr. 2011; and also claims priority to U.S. Provisional Application No. 61/483,008, filed on 5 May 2011. The contents of each of the prior applications are incorporated herein by reference in their entirety.

FIELD OF THE INVENTION

This invention relates to aqueous pharmaceutical formulations containing very low concentrations of a salt of deoxycholic acid ("DCA"), wherein the formulation is maintained at a pH such that precipitation of DCA is substantially inhibited. In a preferred embodiment, the pharmaceutical composition is buffered to maintain a physiologically acceptable pH such that the composition is suitable for injection.

BACKGROUND

Recently published literature reports that the aqueous solutions of DCA has fat removing properties when injected into fatty deposits in vivo (See, WO 2005/117900 and WO 2005/112942, US2005/0261258; US2005/0267080; US2006/127468; and US2006/0154906). DCA injected into fat tissue degrades fat cells via a cytolytic mechanism to provide the desired aesthetic results.

Notwithstanding the benefits of aqueous formulations of DCA, it has been found that at low concentrations of DCA (i.e., less than or about 2% w/v;) in aqueous solutions which optionally contain benzyl alcohol, forms a precipitate after storage over a period of time. Surprisingly, it has been found that the lower the concentration DCA, the higher is the rate of precipitation notwithstanding any significant change in the pH of the solution. This precipitation at very low concentrations is a problem for commercialization as a precipitate is counter-indicated for subcutaneous injections of DCA.

In each treatment regimen, the current clinical trials of aqueous formulations of DCA employ multiple injections of small amounts of the aqueous formulation into different sites defining the fat deposit to be treated.

As it apparent, aqueous formulations of DCA used in such treatments overlap with the problems arising from precipitation of the DCA. That is to say that an initially clear aqueous solution of DCA when stored for a period of time, will form a precipitate at commercially relevant concentrations of DCA notwithstanding the fact that the pH of these solutions are between about 7.50 and about 8.0 which are substantially above the pKa of deoxycholic acid.

Thus, there is a need for stabilizing the low concentration aqueous solutions of deoxycholic acid or a salt thereof against precipitation during a shelf life of at least 2 months.

All publications and patent applications mentioned in this specification are herein incorporated by reference to the same extent as if each individual publication or patent application was specifically and individually indicated to be incorporated by reference.

SUMMARY OF THE INVENTION

It has been surprisingly found that aqueous solutions of a salt of deoxycholic acid at concentrations of from about 0.4% w/v to less than about 2% w/v can be stabilized by adjusting the pH of the solution to above about 8 and preferably from a physiologically acceptable pH from about 8.1 to about 8.5. The pH is preferably maintained within this range by using buffers.

Accordingly, in one of its composition aspects, this invention is directed to aqueous formulations consisting essentially of a salt of deoxycholic acid at a concentration of from about 0.4% w/v to less than about 2% w/v and optionally a preservative effective amount of benzyl alcohol which formulations are stabilized against precipitation by adjusting the pH of the initially formed clear solution to a pH of from about 8.1 to about 8.5.

In another embodiment, this invention is directed to an aqueous formulation consisting essentially of:
  a sterile aqueous solution buffered to a pH of about 8.3;
  about 0.5% w/v or about 1% w/v of a salt of deoxycholic acid;
  optionally a preservative effective amount of benzyl alcohol; and
  about 1% w/v of sodium chloride,
wherein the composition is stable against precipitation.

Also disclosed herein is a method for stabilizing an aqueous composition of a salt of deoxycholic acid against precipitation during storage wherein the concentration of the deoxycholic acid salt is an amount effective to lyse fat cells provided that the amount of the deoxycholic acid salt ranges from about 0.4% w/v to less than 2% w/v, which method comprises:
  forming an aqueous solution of a deoxycholic acid salt at an initial pH above its pKa;
  adjusting the pH of the aqueous solution to a pH of from about 8.1 to about 8.5; and
  optionally including a sufficient amount of buffer to maintain the pH at from about 8.1 to about 8.5.

Also disclosed herein is a method to lyse a fat cell comprising administering to said cell a composition according to this invention.

DETAILED DESCRIPTION

Figure 1:
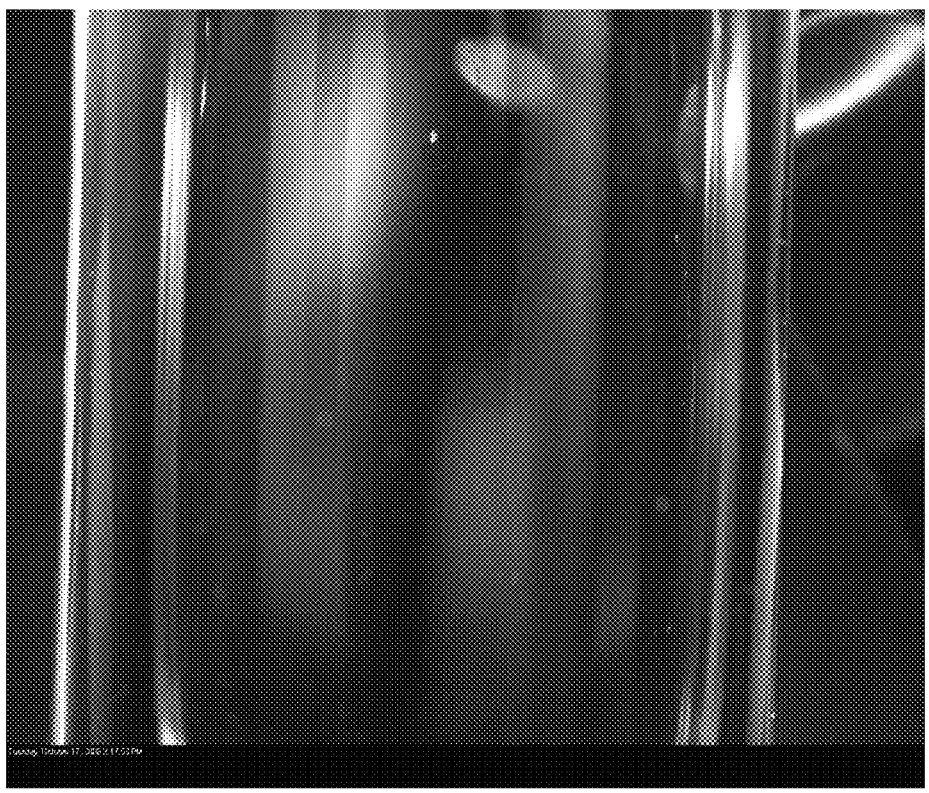
FIG. 1 illustrates (67× enhancement) that an aqueous composition of water and 0.9% w/v benzyl alcohol and no sodium deoxycholate contains only a trace of precipitate, which is presumed to be bioprene tubing particles.

As used herein, certain terms have the following defined meanings.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

As used herein, the term "comprising" is intended to mean that the compositions and methods include the recited elements, but do not exclude others.

"Consisting essentially of" when used to define compositions and methods, shall mean excluding any active ingredients. An "active ingredient" is a substance intended to furnish pharmacological activity or other direct effect in the diagnosis, cure, mitigation, treatment, or prevention of disease or to affect the structure or any function of the human body. Thus, for example, a composition consisting essentially of the elements as defined herein would not exclude trace contaminants from the isolation and purification method and pharmaceutically acceptable carriers, such as phosphate buffered saline, preservatives, and the like but would exclude enzymes such as phosphatases, and proteins. Non-limiting examples of such proteins are heparin, albumin, and the like "Consisting of" shall mean excluding more than trace elements of other ingredients and substantial method steps for administering the compositions of this invention. Embodiments defined by each of these transition terms are within the scope of this invention.

As used herein, the term "salt of deoxycholic acid" or "a salt thereof" refers to pharmaceutically acceptable salts of (4R)-4-((3R,5R,10S,12S,13R,17R)-3,12-dihydroxy-10,13-dimethylhexadecahydro-1H-cyclopenta[a]phenanthren-17-yl)pentanoate having an alkali metal or an ammonium ion as the cation. Preferred are alkali metal salts, with sodium salts being more preferred.

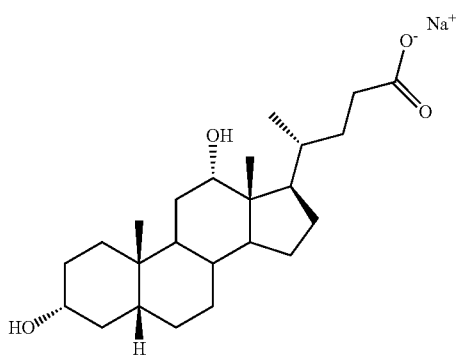

Sodium deoxycholate or sodium (4R)-4-((3R,5R,10S,12S,13R,17R)-3,12-dihydroxy-10,13-dimethylhexadecahydro-1H-cyclopenta[a]phenanthren-17-yl)pentanoate can be prepared according to the methods disclosed in PCT/US2010/061150 titled "Methods for the Purification of Deoxycholic Acid," filed on Dec. 17, 2010, which is hereby incorporated by reference in its entirety.

As used herein, the term "aqueous pharmaceutical formulation" refers to a composition of a deoxycholic acid or a salt thereof in water suitable for administration to a patient preferably via subcutaneous injection from a syringe.

As used herein, the term "buffer" refers to an aqueous solution comprising a mixture of a weak acid and its conjugate base or a weak base and its conjugate acid. A buffer has the property that the pH of the solution changes very little when a small amount of acid or base is added to it. Buffer solutions are used as a means of keeping pH at a nearly constant value in a wide variety of chemical applications. Examples of suitable buffers include phosphate buffers and those known in the literature (see, for example, Troy, D. B., ed. (2005) Remington: The Science and Practice of Pharmacy, 21$^{st}$ ed., Lippincott Williams & Wilkins).

As used herein, the term "base" refers to various typically water-soluble compounds, molecules or ions that in solution have a pH greater than 7. Such compounds, molecules or ions are able to take up a proton from an acid or are able to give up an unshared pair of electrons to an acid. Examples of suitable bases include metal carbonates and bicarbonates, for example sodium carbonate, calcium carbonate, magnesium carbonate, zinc carbonate, sodium bicarbonate and the like; and metal hydroxides, for example sodium hydroxide, potassium hydroxide, and the like, such as those known in the literature (see, for example, Troy, D. B., ed. (2005) Remington: The Science and Practice of Pharmacy, 21$^{st}$ ed., Lippincott Williams & Wilkins).

As used herein, the term "metal carbonates" refers to the metal salt of $CO_3^{2-}$. For example, sodium carbonate, calcium carbonate, magnesium carbonate, zinc carbonate, and the like.

As used herein, the term "metal bicarbonates" refers to the metal salt of $HCO_3^-$. For example, sodium bicarbonate, and the like.

As used herein, the term "metal hydroxides" refers to the metal salt of $^-OH$. For example, sodium hydroxide, potassium hydroxide, and the like.

As used herein, the terms "sterile water" or "water for injection" refer to a sterile, nonpyrogenic preparation of water for injection which contains no bacteriostat, antimicrobial agent or added buffer. In general, the osmolar concentration of additives totals at least 112 mOsm/liter (two-fifths of the normal osmolarity of the extracellular fluid −280 mOsm/liter).

As used herein, the term "benzyl alcohol" refers to the compound

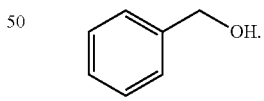

As used herein, the term "precipitation" refers to the formation of a solid in a solution and is readily differentiated from gel formation.

As used herein, the term "solution" refers to a substantially homogeneous mixture comprising two or more substances dissolved in a solvent.

As used herein, the terms "substantially inhibit precipitation" and "inhibits precipitation" means to inhibit most or all visible precipitation so as to maintain homogeneity for a period of time ranging from at least 1 month to at least 1 year.

As used herein, the term "relative standard deviation for homogeneity" or "$H_E$" refers to the value obtained by dividing the standard deviation of the homogeneity by the absolute value of the mean. An $H_E$ less than 10 indicates very good homogeneity.

Formulations

Knowledge about the chemical and physical stability of a drug composition in the desired media for delivery is valuable. In the longer term, the stability of the composition will dictate the shelf life of the marketed product. It is preferable that the active ingredient in a pharmaceutical composition be at the required concentration when administered to a patient.

In the discussion below, sodium deoxycholate is recited for illustrative purposes only and it is understood that other pharmaceutically acceptable salts of deoxycholic acid can be used interchangeably with the sodium salt.

Current clinical methods for the administration of a sodium deoxycholate to a patient to dissolve fat include the administration via subcutaneous injections of a low concentration (i.e., <2% w/v) of an aqueous solution of the salt of deoxycholic acid where the amount of the salt of deoxycholic acid is sufficient to lyse fat cells (about 0.4% w/v and higher). At such concentrations, as it has been shown that the low concentration is beneficial for the effective and safe removal of fat deposits in the body. However, it has been observed that a precipitate forms at such relatively low concentrations of sodium deoxycholate in aqueous media. This precipitation results in a limited shelf life of aqueous solutions of sodium deoxycholate, even at cold temperatures (3-5° C.). In one embodiment, the sodium salt can be replaced by another alkali metal salt.

This instability of aqueous solutions of sodium deoxycholate can be circumvented by the preparation of an aqueous solution of sodium deoxycholate at a concentration of about 5% to about 16% w/v, and having the practitioner dilute the pharmaceutical composition of the sodium deoxycholate solution just prior to use. Whereas this dilution method is effective to allow for both storage stability and effective patient dosing, it is not ideal as a method for routine use especially if a sterile injectable solution of no more than about 2 mL is required. Moreover, current clinical plans include up to 50 injections per treatment session.

It has been found that aqueous formulations of sodium deoxycholate at concentrations ranging from about 0.4% w/v to less than about 2% w/v can be stabilized by adjusting the pH of the solution. This invention is directed to an aqueous formulation consisting essentially of a salt of deoxycholic acid at a concentration ranging from about 0.4% w/v to less than about 2% w/v and optionally a pharmaceutically acceptable excipient such as a preservative effective amount of benzyl alcohol and/or a pH adjusting buffer, wherein said formulation is maintained at a pH of about 8.1 to about 8.5.

In another embodiment, the aqueous formulation is lyophilized to provide for a stable composition which is ready to be reconstituted by addition of the appropriate amount of water. In this embodiment, this invention comprises lyophilized compositions as described above which optionally further contain a lyophilization aid.

In one embodiment, the aqueous formulation contains about 0.5% w/v of a salt of deoxycholic acid. In another embodiment, the aqueous formulation contains about 1% w/v of a salt of deoxycholic acid.

In a further embodiment, the water employed in the aqueous formulation is sterile water. In still a further embodiment, the preservative effective amount of benzyl alcohol is about 0.9% w/v benzyl alcohol and the pH of the formulation is about 8.3. In one embodiment, said salt is an alkali metal salt. In another embodiment, said salt is a sodium salt.

In one embodiment, the pharmaceutical formulations disclosed herein are suitable for injection into a human. The method of injection can be any type of injection, such as subcutaneous injection, as well as other forms of injection.

In one preferred aspect of this invention, the precipitation of the salt of deoxycholic acid in the aqueous formulation is inhibited for a period of at least about six months. In another aspect, the precipitation is inhibited for a period of at least about one year. In yet another aspect, the precipitation is inhibited for a period of at least about two years.

It is contemplated that when stored at various temperatures, for example at ambient or cold temperatures, the formulation can have an increased shelf life. In certain embodiments, the composition is stored at a temperature of from about 17° C. to about 27° C. In some embodiments, the temperature of the formulation is increased to a temperature of about 25° C. to about 37° C. In other embodiments, the formulation is stored at a temperature of from about 2° C. to about 8° C.

In certain embodiments, the pH of the formulation ranges from about 8.1 to about 8.5. In one embodiment, the pH of the composition is about 8.1, or alternatively, about 8.2, or alternatively, about 8.3, or alternatively, about 8.4, or alternatively, about 8.5. In a preferred embodiment, the pH of the formulation is about 8.3.

In one embodiment, the pH is established by the use of a base. It is contemplated that any base can be used to increase the pH of the composition provided that it does not react with the sodium deoxycholate and will not cause harm to the patient. In some embodiments, the base is selected from the group consisting of metal carbonates, metal bicarbonates, metal hydroxides, or a mixture thereof. Examples of bases include, but are not limited to, a base selected from the group consisting of sodium carbonate, calcium carbonate, magnesium carbonate, zinc carbonate, sodium bicarbonate, sodium hydroxide and potassium hydroxide or a mixture thereof. In one embodiment, the base is sodium hydroxide.

In certain cases, the pH of the composition may be maintained at the desired pH during storage with the use of a buffer. Various buffers are known in the art and it is contemplated that any buffer having buffering capacity at the desired pH can be used in the formulations disclosed herein. In one embodiment, the buffer is a phosphate buffer. The amount of phosphate in the composition can be determined to provide a desired pH and salt concentration. In one embodiment, the composition comprises about 10 mM phosphate buffer. In a preferred embodiment, the composition comprises about 10 mM dibasic sodium phosphate buffer.

In some embodiments, the composition comprises at least one excipient to aid in achieving a composition with desired properties, such as increased solubility, preservability or to provide an isotonic solution. Such excipients are known in the art. In one embodiment, the composition comprises about 1% w/v sodium chloride. In another embodiment, the composition comprises about 0.9% w/v benzyl alcohol. In some embodiments, the composition comprises about 0.9% w/v benzyl alcohol and about 1% w/v sodium chloride.

In some embodiments, the pH of the composition is established by use of a base and optionally maintained by use of a buffer.

In a preferred embodiment, this invention provides a stabilized composition comprising:

a phosphate buffer of a pH of about 8.3;

about 0.5% w/v or about 1% w/v of sodium deoxycholate;
a preservative effective amount of benzyl alcohol; and
about 1% w/v of sodium chloride,
wherein the composition is stabilized against precipitation.

In a further embodiment, the phosphate buffer is 10 mM dibasic sodium phosphate buffer.

In one embodiment, the preservative effective amount of benzyl alcohol is about 0.9% w/v.

The formulations disclosed herein comprise from about 0.4% w/v to less than about 2% w/v of a salt of deoxycholic acid in water maintained at a pH sufficient to substantially inhibit precipitation of the salt of deoxycholic acid. The amount of precipitation or homogeneity of the composition can be measured using various methods. For example, it can be measured quantitatively using light scattering by illuminating the composition with a spectrophotometer. Or alternatively, the homogeneity can be measured qualitatively by observing the visual clarity of the solution with the eye. In some embodiments, the composition has a relative standard deviation for homogeneity of less than about 5%. Alternatively, the composition has a relative standard deviation for homogeneity of less than about 4%, or alternatively, about 3%, or alternatively, about 2%, or alternatively, about 1%.

In another embodiment, this invention is directed to a composition consisting essentially of:
a sterile aqueous solution buffered to a pH of about 8.3;
about 0.5% w/v or 1% w/v of sodium deoxycholate;
about 0.9% w/v benzyl alcohol; and
about 1% w/v of sodium chloride,
wherein the composition is stable against precipitation.

In another embodiment, this invention is directed to a composition consisting of:
an aqueous solution buffered to a pH of about 8.3;
about 0.5% w/v or about 1% w/v of sodium deoxycholate;
about 0.9% w/v benzyl alcohol; and
about 1% w/v of sodium chloride,
wherein the composition is stable against precipitation.

In some embodiments, the solutions herein do not include lipids, phospholipids, or phosphatidylcholine. In some embodiments, the solutions herein include up to 5% w/w, w/v, or v/v lipids, specifically phospholipids, or more specifically phosphatidylcholine. Preferably, the amount of lipids used is less than that of sodium deoxycholate or another salt of deoxycholic acid.

In some embodiments, the aqueous pharmaceutical composition of the invention can further comprise a second therapeutic agent selected from the group consisting of: antimicrobial agents, vasoconstrictors, anti-thrombotic agents, anti-coagulation agents, suds-depressants, anti-inflammatory agents, analgesics, dispersion agents, anti-dispersion agents, penetration enhancers, steroids, tranquilizers, muscle relaxants, and anti-diarrhea agents. In some embodiments, a solution is in a container that contains up to 500 mL of solution. Such container can be a syringe or syringe-loadable container.

In some embodiments, the formulations further comprise a molecule known to cause fat to die by an orthogonal mechanism. Such molecules include neuropeptide Y (NPY) antagonists including, but not limited to, NPY receptor antagonists, such as BIBP-3226 (Amgen), BIBO-3304 (Boehringer Ingleheim), BMS-192548 and AR-H040922 (Bristol-Myers Squibb), LY-357897 (Eli Lilly), 1229U91 and GW438014S (GlaxoSmithKline), JNJ-5207787 (Johnson & Johnson), Lu-AA-44608 (Lundbeck), MK-0557 (Merck NPY), NGD-95-1 (Neurgogen), NLX-E201 (Neurologix), CGP-71683 (Novartis), PD-160170 (Pfizer), SR-120819A, BIIE0246, and S.A.0204 (Sanofi Aventis), S-2367 (Shiongli), dihydropyridine and dihydropyridine derivatives that are NPY receptor antagonists, bicyclic compounds that are NPY receptor antagonists, carbazole NPY receptor antagonists, and tricyclic compounds that are NPY receptor antagonists (See, e.g., WO 2006/133160 and U.S. Pat. No. 6,313,128). Also contemplated are fat selective pro-apoptotic peptides such as the CKGGRAKDC peptide that homes to white fat vasculature (See, Kolonin M. G. et al., Nat. Med., 2004, 10(6): 625-32).

Another aspect of the invention relates to mixing adipo-ablative bile acids, such as, deoxycholic acid (DCA) with agents that kill fat cells. In one aspect, this invention contemplates a means to enhance the aesthetic effects of deoxycholate injections by mixing into the deoxycholate injectate a molecule that causes fat to die by an orthogonal mechanism. Examples of such candidate molecules include, but are not limited to, neuropeptide Y (NPY) antagonists and fat selective pro-apoptotic peptides. Since fat cell killing may be required to mediate the desired effects, the effects of an agent with fat killing ability can be enhanced via the addition of a molecule with potent fat cell killing effects. Additionally, molecules that require access to the vasculature to kill (such as certain pro-apoptotic peptides that bind to proteins expressed on the luminal side of capillaries) can gain access to these proteins because deoxycholate may cause vascular leakage. Thus, such agents can be synergistic with deoxycholate potentially creating a more potent means to mediate body contouring in fewer therapeutic sessions.

Examples of NPY antagonists include, but are not limited to, NPY receptor antagonists, such as BIBP-3226 (Amgen), BIBO-3304 (Boehringer Ingleheim), BMS-192548 and AR-H040922 (Bristol-Myers Squibb), LY-357897 (Eli Lilly), 1229U91 and GW438014S (GlaxoSmithKline), JNJ-5207787 (Johnson & Johnson), Lu-AA-44608 (Lundbeck), MK-0557 (Merck NPY), NGD-95-1 (Neurgogen), NLX-E201 (Neurologix), CGP-71683 (Novartis), PD-160170 (Pfizer), SR-120819A, BIIE0246, and S.A.0204 (Sanofi Aventis), S-2367 (Shiongli), dihydropyridine and dihydropyridine derivatives that are NPY receptor antagonists, bicyclic compounds that are NPY receptor antagonists, carbazole NPY receptor antagonists, and tricyclic compounds that are NPY receptor antagonists. See, e.g., WO 2006/133160 and U.S. Pat. No. 6,313,128 (incorporated herein by reference in its entirety including figures).

Exemplary fat selective pro-apoptotic peptides includes, but is not limited to, CKGGRAKDC peptide that homes to white fat vasculature. See, Kolonin M. G. et al., Nat. Med. June 10(6):625-32 (2004).

Sodium deoxycholate or sodium (4R)-4-((3R,5R,10S,12S,13R,17R)-3,12-dihydroxy-10,13-dimethylhexadecahydro-1H-cyclopenta[a]phenanthren-17-yl)pentanoate can be prepared according to the methods disclosed in PCT/US2010/061150 titled "Methods for the Purification of Deoxycholic Acid," filed on Dec. 17, 2010, which is hereby incorporated by reference in its entirety. Other salt of deoxycholic acid s can be prepared likewise by the skilled artisan.

Methods

Disclosed herein are methods for stabilizing an aqueous formulation of deoxycholic acid salt against precipitation during storage wherein the concentration of or a salt thereof is an amount effective to lyse fat cells provided that the amount of salt ranges from about 0.4% w/v to about less than 2% w/v, which method comprises:

forming an aqueous solution of the salt of deoxycholic acid at an initial pH above its pKa;

adjusting the pH of the aqueous solution to a pH of from about 8.1 to about 8.5; and optionally including a sufficient amount of buffer to maintain the pH at from about 8.1 to about 8.5.

In one aspect of this invention, methods disclosed herein substantially stabilize the formulation of deoxycholic acid salt against precipitation over a period of time preferably for at least about six months. In another aspect, the methods stabilize the formulation of deoxycholic acid salt against precipitation for a period of at least about one year. In yet another aspect, the methods stabilize the formulation of deoxycholic acid salt against precipitation for a period of at least about two years.

It has been found that the pH of the solution can inhibit the precipitation of deoxycholic acid or a salt thereof at concentrations of from about 0.4% w/v to less than about 2% w/v in water to allow deoxycholic acid or a salt thereof, to be maintained in solution. In one embodiment, the pH is established by the use of a base. It is contemplated that any base can be used to increase the pH of the composition provided that it does not react with deoxycholic acid or a salt thereof. In some embodiments, the base is selected from the group consisting of metal carbonates, metal bicarbonates, and metal hydroxides, or a mixture thereof. Examples of bases include, but are not limited to, a base selected from the group consisting of sodium carbonate, calcium carbonate, magnesium carbonate, zinc carbonate, sodium bicarbonate, sodium hydroxide and potassium hydroxide or a mixture thereof. In one embodiment, the base is sodium hydroxide.

In certain embodiments, the pH ranges from about 8.1 to about 8.5. In one embodiment, the pH of the composition is about 8.1, or alternatively, about 8.2, or alternatively, about 8.3, or alternatively, about 8.4, or alternatively, about 8.5. In a preferred embodiment, the pH of the aqueous solution is about 8.3.

In certain cases, the pH of the composition may need to be maintained with the use of a buffer. Various buffers are know in the art and it is contemplated that any buffer having buffering capacity at the desired pH can be used in the formulations disclosed herein. In one embodiment, the buffer is a phosphate buffer. The amount of phosphate required to provide a desired pH and salt concentration can be calculated using methods well known in the art. In one embodiment, the composition comprises about 10 mM phosphate buffer. In another embodiment, the phosphate buffer is 10 mM dibasic sodium phosphate buffer.

In certain cases, the pH is established by use of a base and optionally maintained by use of a buffer.

In one embodiment, the methods disclosed herein provide formulations which are suitable for injection into a human. The method of injection can be any type of injection, such as subcutaneous injection, as well as other forms of injection. Therefore, in some embodiments, the aqueous solution comprises sterile water or water for injection (WFI).

In one aspect, it may be that one or more excipients are used to maintain the solubility, or increase the preservability of deoxycholic acid salt present in the formulation. In one embodiment, the method comprises adding about 1% w/v benzyl alcohol. In some embodiments, the formulation also comprises at least one excipient to aid in achieving an isotonic solution. Such excipients are known in the art. In one embodiment, the method comprises adding about 1% w/v sodium chloride. In some embodiments, the method comprises adding both 1% w/v benzyl alcohol and 1% w/v sodium chloride. In some embodiments, the method comprises adding both 0.9% w/v benzyl alcohol and 0.9% w/v sodium chloride. Using the methods disclosed herein, an aqueous solution comprising less than about 2% w/v of deoxycholic acid salt is maintained at a pH sufficient to substantially inhibit precipitation of deoxycholic acid salt. The amount of precipitation or homogeneity of the composition can be measured using various methods. For example, it can be measured quantitatively by measuring the light scattering via illumination by a spectrophotometer. Or alternatively, the homogeneity can be measured qualitatively by simply observing the visual clarity of the solution with the eye. In some embodiments, the method provides a pharmaceutical composition having a relative standard deviation for homogeneity of less than about 5%. Alternatively, the relative standard deviation for homogeneity of less than about 4%, or alternatively, about 3%, or alternatively, about 2%, or alternatively, about 1%.

The storage temperature can assist in maintaining the solubility of deoxycholic acid salt in the formulation. In certain embodiments, the storage temperature is from about 17° C. to about 27° C. In some embodiments, the storage temperature is about 25° C. to about 37° C. In other embodiments, the storage temperature is from about 2° C. to about 8° C.

It is contemplated that the concentration of the salt of deoxycholic acid in the formulation is about 0.5% w/v, or alternatively about 0.7% w/v, or alternatively about 1% w/v, or alternatively about 1.2% w/v, or alternatively about 1.4% w/v, or alternatively less than about 2% w/v. In a preferred embodiment, the salt of deoxycholic acid is sodium deoxycholate. In another preferred embodiment, the composition comprises 0.5% w/v of sodium deoxycholate. In another preferred embodiment, the composition comprises 1% w/v of sodium deoxycholate.

In one embodiment, the aqueous formulation is split into a plurality of individual solutions which are separately administered to the fat cells. For example, the aqueous formulation is split into 5, 10, 15, 20, 25 or 30 separate solutions and, in some cases, up to 50 separate solutions.

In a preferred embodiment, the salt of deoxycholic acid is sodium deoxycholate. As the methods of this invention include subcutaneous injections, there is also provided a syringe comprising a chamber, a plunger and an injection needle wherein the chamber comprises a formulation of this invention. Preferably, the chamber is sufficient to hold at least 2 mL and preferably no more than 4 mL of the formulation.

In another embodiment, this invention provides a synthesis of DCA from protected commercially available 9-α,17-β-dihydroxy-5-α-androstan-3-one as shown in scheme 1 below.

Scheme 1: Synthesis of DCA

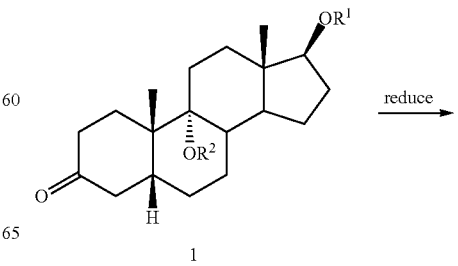

1

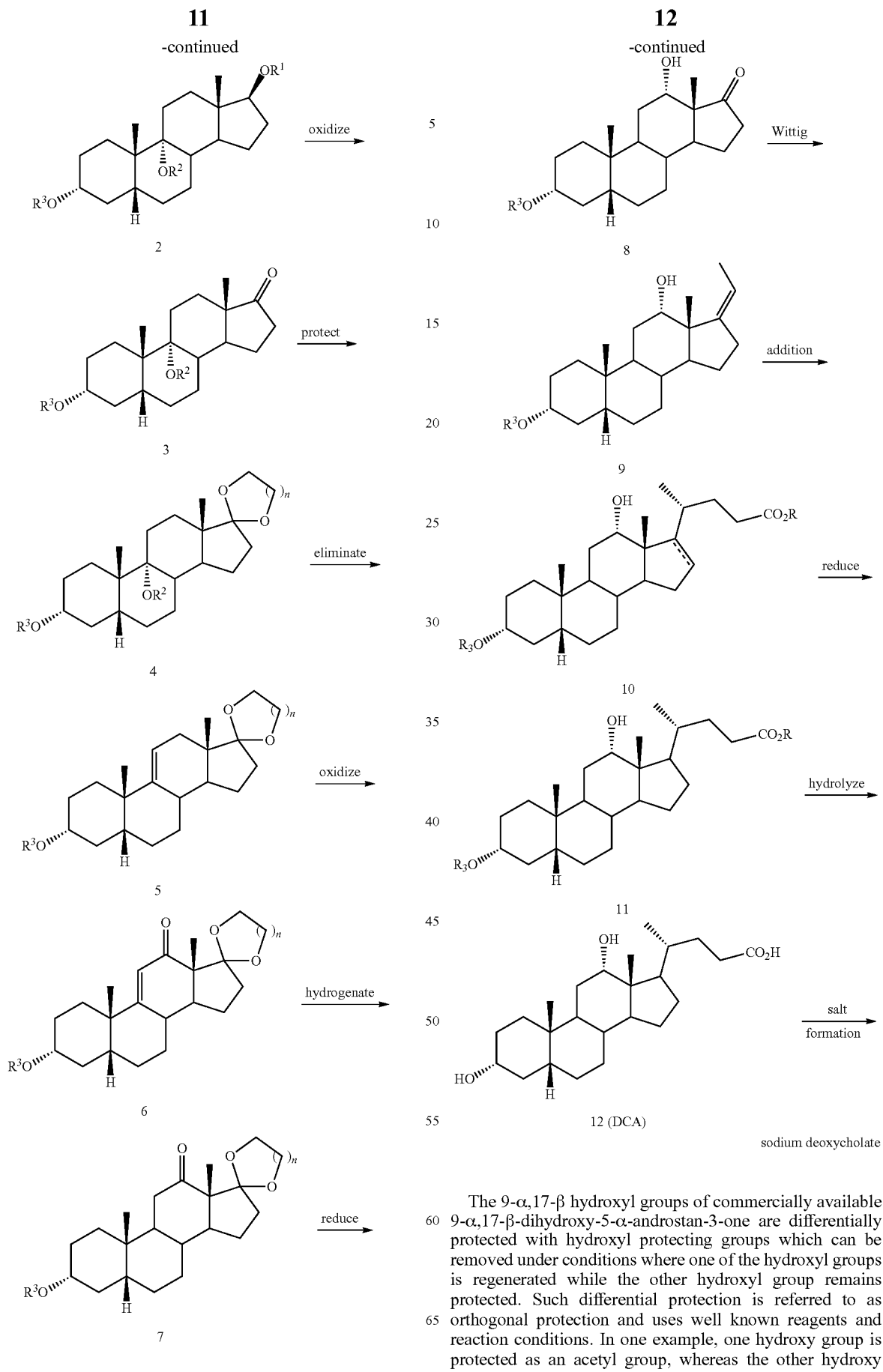

sodium deoxycholate

The 9-α,17-β hydroxyl groups of commercially available 9-α,17-β-dihydroxy-5-α-androstan-3-one are differentially protected with hydroxyl protecting groups which can be removed under conditions where one of the hydroxyl groups is regenerated while the other hydroxyl group remains protected. Such differential protection is referred to as orthogonal protection and uses well known reagents and reaction conditions. In one example, one hydroxy group is protected as an acetyl group, whereas the other hydroxy group is protected as a benzyl group. Each group can be selectively removed under reaction conditions that retain the other hydroxyl protecting group intact.

It is contemplated that the relatively sterically protected 9-α-hydroxyl group may not need to be protected as the reactions contemplated prior to elimination of that group are likely inhibited at this position due to steric hindrance. Regardless, protection of this hydroxyl group adequately insures that the group remains intact until elimination of the hydroxyl group via dehydration is desired.

The 3-one group of orthogonally protected 9-α,17-β-dihydroxy-5-α-androstan-3-one, compound 1, is reduced with conventional reducing agent such as sodium borohydride to provide the 3-α-hydroxy derivative which is then protected with yet another orthogonal protecting group to provide compound 2.

The hydroxyl protecting group at the 17-position of compound 2 is then selectively removed and the hydroxyl group so regenerated is then oxidized with a suitable oxidation reagent such as $CrO_3$ to provide the 17-keto derivative, compound 3. The 17-keto group in compound 3 is protected as a ketal under standard ketalization conditions such as reaction with 1,2-dihydroxyethane or 1,3-dihydroxypropane to give compound 4 (which illustrates ketal formation with the 1,2-dihydroxyethane for illustrative purposes only).

Deprotection of the 9-α-hydroxyl as necessary is followed by dehydration of that hydroxyl group under conditions such as acid-catalyzed elimination provides the 9,10-unstaurated derivative, compound 5. Generation of a 12-keto group is accomplished by allylic oxidation of compound 5 with oxidation reagents such as chromic acid or TBHP (tert-butyl hydroperoxide) and NaOCl to provide compound 6. See, for example, U.S. Patent Application Ser. No. 61/348,686 which is incorporated herein by reference in its entirety. Alternatively, the allylic oxidation is accomplished by using about 2 to 5 equivalents of TBHP and about 0.3 to 0.5 equivalents of CuI as a catalyst. The reaction is carried out in a solvent such as acetonitrile at 40° C. for about 40-55 hours. The slow portionwise addition of TBHP results in more efficient oxidation. The product formed contains a mixture of compound 6 and the corresponding allylic alcohol. The product mixture is then oxidized with PCC to give compound 6.

Hydrogenation of compound 6 under standard conditions such as 10% Pd/C and $H_2$ provides compound 7. Reduction of the 12-keto group in compound 7 with reagents such as LiAl(OBu$^t$)$_3$H provides the 12-hydroxy derivative, compound 8. Olefination of compound 8 under standard Wittig conditions such as using ethyltriphenylphosphonium bromide in presence of a base such as potassium tert-butoxide provides compound 9. Addition of an alkyl acrylate such as methyl acrylate in presence of a Lewis acid provides compound 10, wherein R is an alkyl group such as methyl. Reduction of the double bond in compound 10 again proceeds under standard hydrogenation conditions such as Pd/C and $H_2$ to provide compound 11. Deprotection of the 3-OR$_3$ followed by hydrolysis with a base such as LiOH provides DCA, compound 12.

Compound 12 (crude DCA) was further purified with methanol wash and recrystallized from ethanol. It was diluted with 2 mol % MeOH in $CH_2Cl_2$ (25 vol) and heated to 35-37° C. for 1 hour. The slurry was allowed to cool to 28-30° C. and filtered. The filter cake was washed with $CH_2Cl_2$ (5 vol) and dried under vacuum at 40° C. to afford DCA.

DCA was dissolved in 10% DI water/EtOH (12 vol), polish filtered over celite and washed with 10% DI water/EtOH (3 vol). The resulting 15 volume filtrate was added to DI water (30 vol) and a thin white slurry was afforded. The slurry was held for 24 hours, filtered, washed with DI water (20 vol) and dried under vacuum at 40° C. to afford DCA.

Conversion of DCA to a pharmaceutically acceptable salt such as sodium deoxycholate proceeds via conventional conditions. Alternatively, conversion of a pharmaceutically acceptable salt of DCA such as sodium deoxycholate to DCA also proceeds via conventional conditions.

In another embodiment, this invention provides a stabilized formulation comprising:
  a buffered aqueous solution having a pH of about 8.1 to about 8.5 and further comprising about 0.5% of sodium deoxycholate and about 0.9% of benzyl alcohol,
wherein the formulation is stabilized against precipitation, and the sodium deoxycholate is prepared according to scheme 1.

In another embodiment, this invention provides a stabilized formulation comprising:
  a buffered aqueous solution having a pH of about 8.1 to about 8.5 and further comprising about 1% of sodium deoxycholate and about 0.9% of benzyl alcohol,
wherein the formulation is stabilized against precipitation, and the sodium deoxycholate is prepared according to scheme 1.

EXAMPLES

In the examples and elsewhere in the specification, abbreviations have the following meanings:
Mg=Milligram
mL=Milliliter
Mm=Millimeter
mM=Millimolar
T=Time
UV=Ultraviolet
v/v=Volume/Volume
w/v=Weight/Volume (g/mL)
w/w=Weight/Weight
WFI=Water for Injection
mOsm=Milliosmole The invention is further understood by reference to the following examples, which are intended to be purely exemplary of the invention. This invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description. Although several embodiments of the invention are described herein in detail, it will be understood by those skilled in the art that variations may be made thereto without departing from the spirit of the invention or the scope of the appended claims. Such modifications fall within the scope of the appended claims.

Example 1

Concentration Dependent Precipitation from a Solution of Sodium Deoxycholate

Figure 2:
FIG. 2 illustrates (67× enhancement) that an aqueous composition of water, 0.5% w/v sodium deoxycholate and 0.9% w/v benzyl alcohol contains significant amounts of precipitate which is presumed to be deoxycholate crystals.
Figure 3:
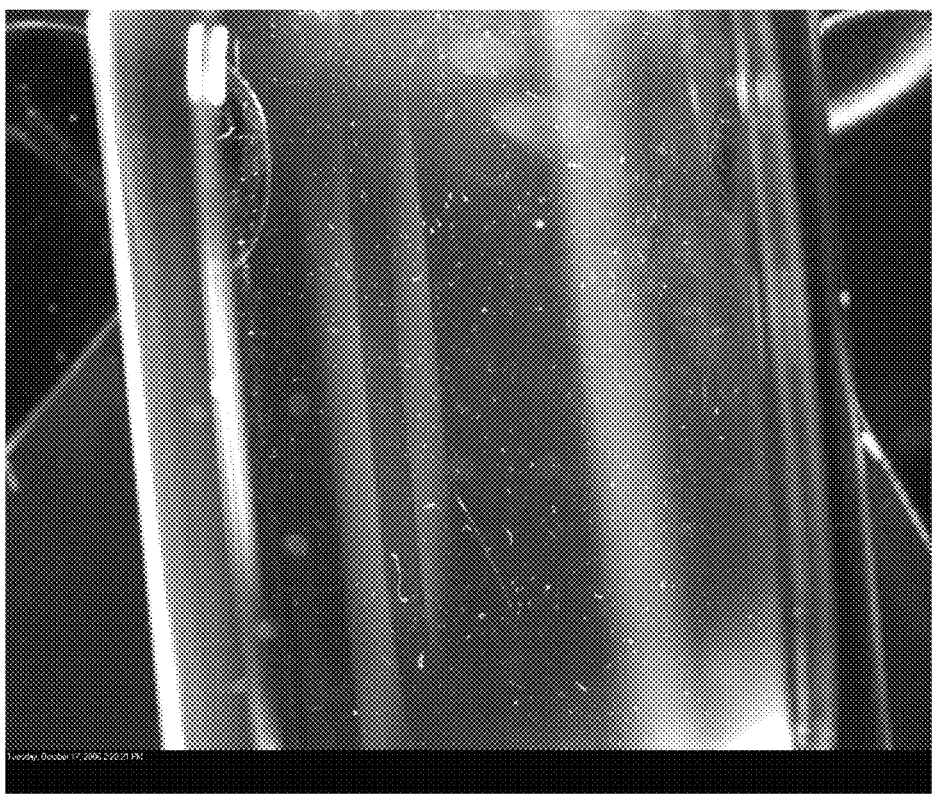
FIG. 3 illustrates (67× enhancement) that an aqueous composition of water, 1% w/v sodium deoxycholate and 0.9% w/v benzyl alcohol contains significant amounts of precipitate, albeit less than that of 0.5% w/v sodium deoxycholate. As before, the precipitate is presumed to be deoxycholate crystals.
Figure 4:
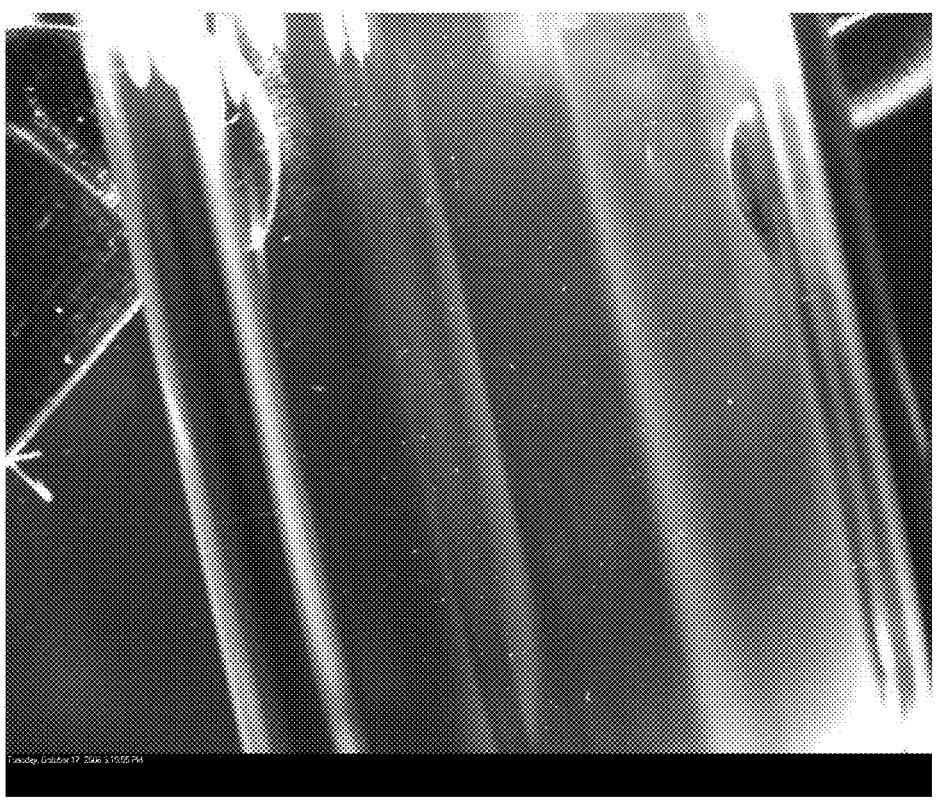
FIG. 4 illustrates (67× enhancement) that an aqueous composition of water, 2% w/v sodium deoxycholate and 0.9% w/v benzyl alcohol contains significant amounts of precipitate but substantially less than that observed in FIGS. 2 and 3.

Solutions of sodium deoxycholate at different concentration were evaluated for precipitate formation after 1 week of storage. The results are depicted in FIGS. 1-4, and demonstrate that at about 0.5% and at about 1% (w/v) concentration of sodium deoxycholate in an aqueous solution containing only water and 0.9% w/v benzyl alcohol, a significant amount of precipitate is formed such that it would inhibit use of the solution as a composition for subcutaneous injections. By visual inspection of FIGS. 1-4, the amount of precipitation can be rated as tabulated below.

TABLE 1

| % w/v Sodium Deoxycholate | Precipitation Rating | Comment |
|---|---|---|
| 0 | 1 | Precipitation substantially invisible to the naked eye |
| 0.5 | 10 | Significant amounts of precipitate visible to the naked eye |
| 1.0 | 7 | Significant amounts of precipitate visible to the naked eye but less than that for 0.5% w/v |
| 2.0 | 2 | Precipitation visible to the naked eye but present in substantially smaller amounts compared to the 0.5 and 1% solutions above |

The precipitation rating estimates that "0" refers a clear solution and that "10" refers to a mixture exhibiting substantial precipitation readily visible to the naked eye.

Such an observation demonstrates that in the concentration ranges tested, the precipitation phenomena was substantially affected by deoxycholate concentration. To ascertain pH's effect on precipitation, the pH of the solutions were measured, as provided in Table 2, which demonstrates that the pH of the solutions were substantially the same, especially for the 1% and the 2% solutions. The inverse aqueous solubility of sodium deoxycholate, where a more dilute solution (0.5% or 1%) provides more precipitation than a more concentrated solution (2%), is a surprising observation and also evidences that the precipitation phenomena is not directly related to pH, because the pH of the solutions were substantially the same again, especially for the 1% and 2% solutions.

TABLE 2

| % w/v Sodium Deoxycholate | Reading # | Temperature/° C. | pH |
|---|---|---|---|
| 0 | 1 | 24.0 | 7.75 |
| 0 | 2 | 24.1 | 7.58 |
| 0.5 | 1 | 24.7 | 7.77 |
| 0.5 | 2 | 24.5 | 7.71 |
| 1 | 1 | 24.6 | 7.93 |
| 1 | 2 | 24.5 | 7.97 |
| 2 | 1 | 24.9 | 8.07 |
| 2 | 2 | 24.7 | 8.06 |

Accordingly, this invention provides that the surprising precipitation from dilute, 0.4% to less than 2% (w/v), salt of deoxycholic acid solutions are inhibited, to the extent that such solutions are useful for subcutaneous injections, by increasing the solution pH.

Example 2

Sodium Deoxycholate (API) Formulations with and without Benzyl Alcohol

1. A composition of sodium deoxycholate (0.5% and 1%) was prepared comprising sodium phosphate (10 mM), sodium chloride (75-90 mM), benzyl alcohol (0.9%), deoxycholic acid, pH 8.3.

2. An isotonic composition of sodium deoxycholate without benzyl alcohol was prepared using the free acid form, namely, deoxycholic acid, as follows.

a. Preparation of 100 mL Isotonic Batches at 10 mg/mL 1.0 g of the deoxycholic acid (DCA) added to the solution only after a basic solution was made with 70 mL water, 142 mg anhydrous dibasic sodium phosphate and 267 µL 10M NaOH. It took about 20 minutes for the API to go into solution. The pH of the solution was 11.1. The rapid addition of HCl was known to cause some precipitation, so 225 µL of 1M HCl was slowly added to bring the solution to pH 8.3. The solution was allowed to mix for an additional 15 minutes. After bringing the volume up to 100 mL with water, the osmolality was found to be 51 mOsm. Addition of 859 mg of NaCl brought the osmolality up to 305 mOsm.

The solution so prepared could optionally be lyophilized to provide for a lyophilized product which could be reconstituted by addition of the appropriate amount of sterile water. Accordingly, this invention also provides for lyophilized products of the solutions disclosed herein.

b. Preparation of 1000 mL Isotonic Batches at 10 mg/mL

The results from section a (above) did not scale up perfectly when multiplied ten fold. To 900 mL of water, 1.4 g anhydrous dibasic sodium phosphate, 8.6 g NaCl, and 2.7 mL 10 M NaOH were added. 10.0 g of DCA was then added and allowed to mix to clarity for 30 minutes. The pH of the solution was 10.4. 1.5 mL 1 M HCl was slowly added and allowed to mix for 5 minutes. The final pH was 8.1. An additional 20 µL of 10M NaOH had to be added to bring the pH to 8.3. After bringing the volume up to 1000 mL with water, the osmolality was 314 mOsm.

Based on observations of the pH change during the addition of 1 M HCl, it was determined that for 1000 mL batches at 10 mg/mL API, just 1.0 mL of 1M HCl should be immediately added and then slowly titrated with small volumes of the acid. The suggested order of addition for 1000 mL of 10 mg/mL API is outlined in Table 3.

c. Preparation of 100 mL Isotonic Batches at 5 mg/mL 0.50 g of deoxycholic acid (DCA) was added to the solution only after a basic solution was made with 70 mL water, 142 mg anhydrous dibasic sodium phosphate and 134 µL 10M NaOH. It took about 20 minutes for the API to go into solution. The pH was 10.7. The rapid addition of HCl was known to cause some precipitation, so 115 µL of 1 M HCl was slowly added to bring the solution to pH 8.3. The solution was allowed to mix for an additional 15 minutes. After bringing the volume up to 100 mL with water, the osmolality was found to be 39 mOsm. Addition of 859 mg of NaCl brought the osmolality up to 294 mOsm.

d. Preparation of 1000 mL Isotonic Batches at 5 mg/mL

The results from section c (above) did not scale up perfectly when multiplied ten fold. To 900 mL of water, 1.4 g anhydrous dibasic sodium phosphate, 8.6 g NaCl, and 1.3 mL 10M NaOH were added. 5.0 g of DCA was then added and allowed to mix to clarity for 30 minutes. The pH was 8.6. After adding just 350 µL 1M HCl, the pH dropped to 8.0. An additional 25 µL of 10M NaOH had to be added to bring the pH to 8.4. After bringing the volume up to 1000 mL with water, the osmolality was 305 mOsm. Based on observations of the pH change during the addition of 1 M HCl, it was determined that for 1000 mL batches at 5 mg/mL API, that the solution should be slowly titrated with small volumes of 1M HCl. The suggested order of addition for 1000 mL of 5 mg/mL is outlined in Table 3.

TABLE 3

Order of addition (left to right) for isotonic 1000 mL benzyl alcohol free formulation

| API Concentration | Dibasic Annhydrous Sodium Phosphate | 10M NaOH | DCA | NaCl | 1M HCl | pH |
|---|---|---|---|---|---|---|
| 10 mg/mL | 1.4 g | 2.7 mL | 10.0 g | 8.6 g | 1.0 mL + incremental addition to final pH | 8.3 |
| 5 mg/mL | 1.4 g | 1.3 mL | 5.0 g | 8.6 g | incremental addition to final pH | 8.3 |

What is claimed is:

1. A method for stabilizing an aqueous composition of a salt of deoxycholic acid against precipitation during storage, which method comprises:
   a) forming an aqueous solution of the salt of deoxycholic acid;
   b) adjusting the pH of the aqueous solution to a pH of from about 8.1 to about 8.5 thereby stabilizing said composition against precipitation during storage; and
   c) and forming the aqueous composition consisting of the salt of deoxycholic acid at a concentration ranging from about 0.4% w/v to less than 2% w/v and at least one pharmaceutically acceptable excipient and/or carrier.

2. The method of claim 1, wherein said salt is the sodium salt of deoxycholic acid.

3. The method of claim 1, wherein the pH of the aqueous solution is maintained at about 8.3.

4. The method of claim 3, wherein said salt is the sodium salt of deoxycholic acid.

5. The method of claim 1, wherein the pH is maintained at from about 8.1 to about 8.5.

6. The method of claim 5, wherein the pH is maintained with a sufficient amount of buffer.

* * * * *